(12) United States Patent
Barker

(10) Patent No.: US 7,899,548 B2
(45) Date of Patent: Mar. 1, 2011

(54) LEAD WITH CONTACTS FORMED BY COILED CONDUCTOR AND METHODS OF MANUFACTURE AND USE

(75) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 398 days.

(21) Appl. No.: 11/773,867

(22) Filed: Jul. 5, 2007

(65) Prior Publication Data

US 2009/0012591 A1 Jan. 8, 2009

(51) Int. Cl.
*A61N 1/08* (2006.01)

(52) U.S. Cl. .............................. 607/116; 607/45; 607/46

(58) Field of Classification Search ............... 607/1–25, 607/116–126; 600/374, 377, 508; 604/506; 128/418–419
See application file for complete search history.

(56) References Cited

U.S. PATENT DOCUMENTS

| | | | |
|---|---|---|---|
| 3,788,329 A * | 1/1974 | Friedman | 607/122 |
| 4,161,952 A * | 7/1979 | Kinney et al. | 607/122 |
| 4,280,511 A | 7/1981 | O'Neill | |
| 4,559,951 A | 12/1985 | Dahl et al. | |
| 4,840,186 A | 6/1989 | Lekholm et al. | |
| 5,007,435 A | 4/1991 | Doan et al. | |
| 5,111,812 A * | 5/1992 | Swanson et al. | 607/2 |
| 5,458,629 A | 10/1995 | Baudino et al. | |
| 5,466,253 A | 11/1995 | Doan | |
| 5,522,872 A * | 6/1996 | Hoff | 607/119 |
| 5,584,873 A | 12/1996 | Shoberg et al. | |
| 5,658,263 A | 8/1997 | Dang et al. | |
| 5,658,709 A | 8/1997 | Layman et al. | |
| RE35,924 E | 10/1998 | Winkler | |
| 5,855,552 A * | 1/1999 | Houser et al. | 600/374 |
| 5,869,804 A | 2/1999 | Mueller et al. | |
| 5,935,159 A | 8/1999 | Cross, Jr. et al. | |
| 6,052,625 A | 4/2000 | Marshall | |
| 6,066,166 A | 5/2000 | Bischoff et al. | |
| 6,076,017 A | 6/2000 | Taylor et al. | |
| 6,167,314 A | 12/2000 | Fischer, Sr. et al. | |
| 6,181,969 B1 | 1/2001 | Gord | |
| 6,208,881 B1 | 3/2001 | Champeau | |
| 6,216,045 B1 | 4/2001 | Black et al. | |
| 6,249,708 B1 | 6/2001 | Nelson et al. | |
| 6,253,111 B1 | 6/2001 | Carner | |
| 6,259,954 B1 * | 7/2001 | Conger et al. | 607/122 |
| 6,326,587 B1 | 12/2001 | Cardineau et al. | |
| 6,366,820 B1 | 4/2002 | Doan et al. | |
| 6,430,442 B1 | 8/2002 | Peters et al. | |
| 6,434,430 B2 | 8/2002 | Borgersen et al. | |
| 6,440,488 B2 | 8/2002 | Griffin, III et al. | |

(Continued)

OTHER PUBLICATIONS

U.S. Appl. No. 11/238,240, filed Sep. 29, 2005 (20 pages).
U.S. Appl. No. 11/609,586, filed Dec. 12, 2006 (23 pages).

*Primary Examiner*—Carl H. Layno
*Assistant Examiner*—Paula J Stice
(74) *Attorney, Agent, or Firm*—Frommer Lawrence & Haug LLP; Bruce E. Black

(57) ABSTRACT

A lead includes an elongated lead body of non-conductive material and a plurality of conductive wires. Each wire has a first portion disposed within the lead body and a second portion extending out of the lead body. The second portion is coiled around the lead body to form a contact on the outer surface of the lead.

19 Claims, 6 Drawing Sheets

U.S. PATENT DOCUMENTS

| | | | |
|---|---|---|---|
| 6,477,427 B1 * | 11/2002 | Stolz et al. | 607/116 |
| 6,505,401 B1 | 1/2003 | Doan | |
| 6,516,227 B1 | 2/2003 | Meadows et al. | |
| 6,516,230 B2 * | 2/2003 | Williams et al. | 607/116 |
| 6,516,232 B2 | 2/2003 | Skinner | |
| 6,609,029 B1 | 8/2003 | Mann et al. | |
| 6,609,032 B1 | 8/2003 | Woods et al. | |
| 6,697,675 B1 * | 2/2004 | Safarevich et al. | 607/116 |
| 6,725,096 B2 | 4/2004 | Chinn et al. | |
| 6,741,892 B1 | 5/2004 | Meadows et al. | |
| 6,757,970 B1 | 7/2004 | Kuzma et al. | |
| 6,908,442 B2 | 6/2005 | von Malmborg et al. | |
| 6,952,616 B2 | 10/2005 | Wessman et al. | |
| 6,981,314 B2 | 1/2006 | Black et al. | |
| 7,039,470 B1 | 5/2006 | Wessman | |
| 7,047,081 B2 | 5/2006 | Kuzma | |
| 7,047,082 B1 | 5/2006 | Schrom et al. | |
| 7,047,627 B2 | 5/2006 | Black et al. | |
| 7,051,419 B2 | 5/2006 | Schrom et al. | |
| 7,571,010 B2 * | 8/2009 | Zarembo et al. | 607/115 |
| 2002/0032468 A1 * | 3/2002 | Hill et al. | 607/2 |
| 2004/0059392 A1 | 3/2004 | Parramon et al. | |
| 2005/0027341 A1 * | 2/2005 | Schrom et al. | 607/116 |
| 2005/0208095 A1 | 9/2005 | Hunter et al. | |
| 2007/0027514 A1 | 2/2007 | Gerber | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0219595 A1 | 9/2007 | He | |
| 2007/0239243 A1 | 10/2007 | Moffitt et al. | |

* cited by examiner

LEAD WITH CONTACTS FORMED BY COILED CONDUCTOR AND METHODS OF MANUFACTURE AND USE

FIELD

The present invention is directed to the area of leads for implantable devices and the method of manufacture and use of the leads. In addition, the present invention is also directed to the area of leads with coiled conductors and implantable devices containing the leads.

BACKGROUND

Implantable stimulation systems have been developed to provide therapy for a variety of disorders, as well as for other treatments. For example, stimulation systems can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

As one example, spinal cord stimulation is a well accepted clinical method for reducing pain in certain populations of patients. Stimulation systems have been developed to provide therapy for a variety of treatments. For example, stimulation systems can be used to stimulate nerves, such as the spinal cord, muscles, or other tissue. A stimulation system can include a control module (with a pulse generator) and one or more leads. Each lead can include an array of electrodes near a distal end of the lead and an array of control module contacts near a proximal end of the lead. The electrodes are in contact with or near the nerves, muscles, or other tissue to be stimulated. The control module contacts are in contact with corresponding contacts in the control module. The pulse generator in the control module generates electrical pulses that are transmitted through the control module/lead contacts, the lead, and the electrode for delivery to body tissue. As an example, electrical pulses can be provided to the dorsal column fibers within the spinal cord to provide spinal cord stimulation.

BRIEF SUMMARY

One embodiment is a lead including an elongated lead body of non-conductive material and a plurality of conductive wires. Each wire has a first portion disposed within the lead body and a second portion extending out of the lead body. The second portion is coiled around the lead body to form a contact on the outer surface of the lead.

Another embodiment is a stimulation system including the lead described above and a control module coupleable to the lead, where the control module is arranged to provide electrical signals to the contact.

Yet another embodiment is a method of producing a lead including disposing a conductive wire within, and along, an elongated lead body with a terminal portion of the wire extending through an opening at, or near, a first end of the lead body. The terminal portion of the conductive wire is coiled around the lead body to form a contact.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of leads for implantable devices and the method of manufacture and use of the leads. In addition, the present invention is also directed to the area of electrical contacts between the leads and the implantable devices and between the leads and biological tissue.

Figure 1:
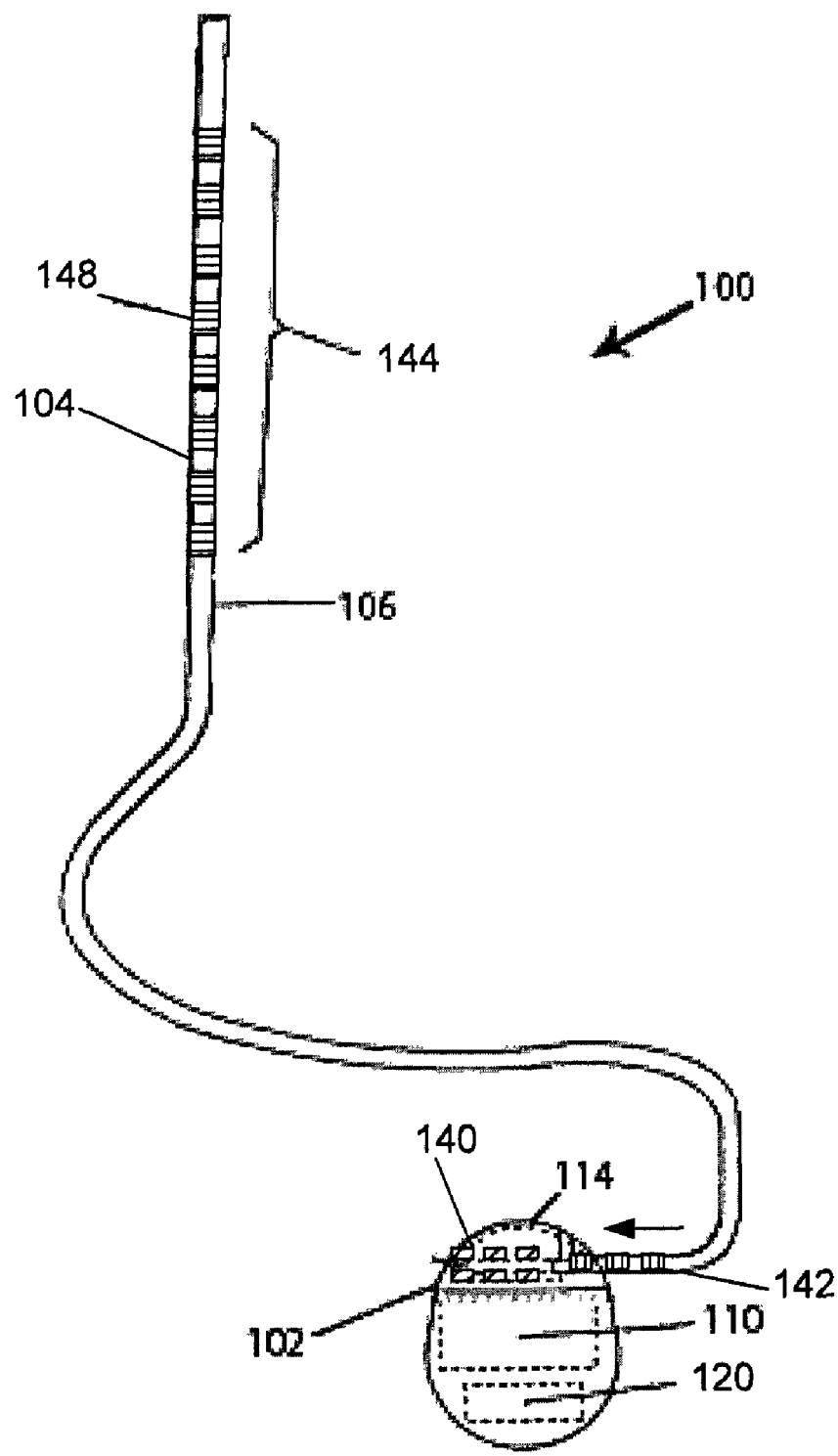
FIG. 1 is a schematic illustration of one embodiment of a stimulation system, according to the invention.

FIG. 1 illustrates schematically one embodiment of a stimulation system 100. The stimulation system includes a control module (e.g., a stimulator or pulse generator) 102 and at least one lead 104. The control module 102 typically includes a housing 114 with an electronic subassembly 110 and, in at least some embodiments, a power source 120. The control module 102 further includes a control module contact array 140. The lead 104 includes a lead body 106 and a lead contact array 142 with contacts which are arranged to couple with corresponding contacts of the control module contact array 140. The lead 104 also includes a lead electrode array 144 that includes contacts that form electrodes 148 for tissue stimulation. Any type of lead and electrode arrangement can be used including, but not limited to, percutaneous leads (as shown in FIG. 1), paddle leads, and cuff leads.

It will be understood that the system for stimulation can include more, fewer, or different components and can have a variety of different configurations including those configurations disclosed in the stimulation system references cited herein. Examples of stimulation systems with leads are found in, for example, U.S. Pat. Nos. 6,181,969; 6,516,227; 6,609,029; 6,609,032; and 6,741,892; and U.S. patent application Ser. Nos. 11/238,240; 11/319,291; 11/327,880; 11/375,638; 11/393,991; 11/396,309; and 11/609,586, all of which are herein incorporated by reference.

The stimulation system or components of the stimulation system, including one or both of the lead 104 and the control module 102, are typically implanted into the body. The stimulation system can be used for a variety of applications including, but not limited to, brain stimulation, neural stimulation (e.g., spinal cord stimulation), muscle stimulation, and the like.

Figure 2:
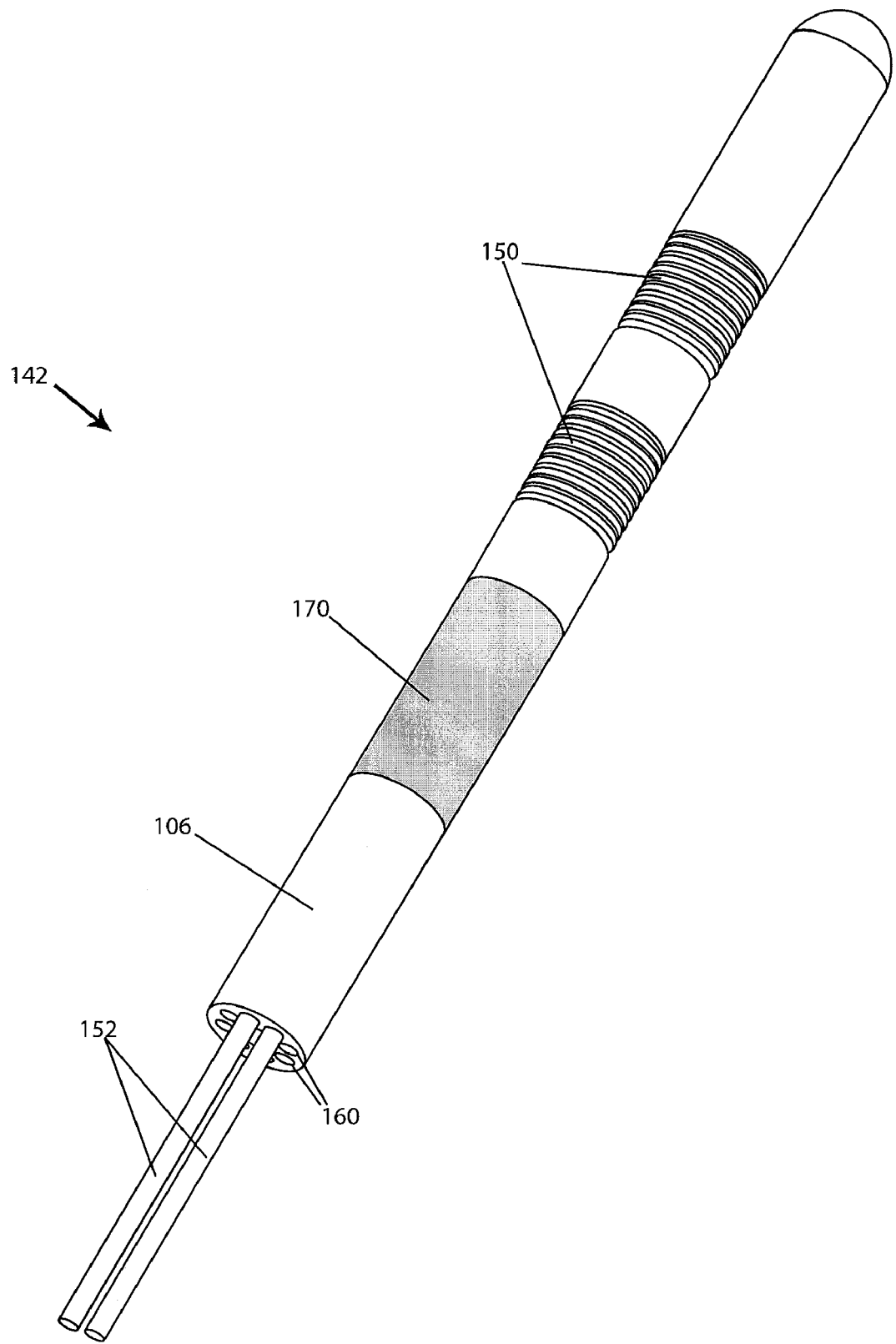
FIG. 2 is a schematic perspective view of a portion of one embodiment of a lead, according to the invention.

FIG. 2 illustrates a schematic perspective view of a portion of one embodiment of a lead 104, according to the invention. Lead 104 includes a lead contact array 142 which is composed of an array of contacts 150 that are disposed about the lead body 106 and are preferably located near the proximal end of the lead 104. Contacts at a proximal end of the lead can form the lead contact array 142 of FIG. 1 and can make contact with corresponding contacts in the control module contact array 140 (FIG. 1) of the control module.

Alternatively, the lead 104 can be attached to a lead extension (not shown) which is in turn attached to the control module (or even another lead extension.) The lead extension is typically similar to the lead 104 except that it is configured for attachment to the lead (or another lead extension) at the distal end and for attachment to the control module (or another lead extension) at the proximal end. The contacts 150 of the lead contact array 142 can make contact with corresponding contacts on the lead extension. In another embodiment, a lead extension can include contacts 150 as described herein on a proximal end for coupling to contacts on a control module or another lead extension.

In addition, contacts 150 can be formed by coiling portions of conductors 152, as described below, and disposed at a distal end of the lead to act as electrodes 148 of FIG. 1, if desired, particularly for percutaneous leads. Alternatively, other known percutaneous electrode arrangements can be used.

Each of the contacts 150 can be made by coiling a terminal portion of a conductor 152 about the lead body 106. The conductors 152 typically run the length of the lead connecting the electrodes 148 to the contacts of the lead contact array 142. The conductors 152 are used to make either the contacts of the lead contact array 142, the electrodes 148, or both. Otherwise, conventional contacts or electrodes (e.g., ring contacts or ring electrodes) can be used. Typically, most, if not all, of the contacts of the lead contact array 142 are individually coupled by the conductors 152 to one or more of the electrodes 148. In some embodiments, the contacts of the lead contact array 142 are coupled to, at most, only one of the electrodes 148. Such an arrangement allows for independent operation of each of the electrodes. In other embodiments, it may be desirable to have one or more of the contacts of the lead contact array 142 coupled to more than one of the electrodes 148.

The lead body 106 may define one or more lumens 160 along which the conductors 152 can be disposed. Alternatively, the conductors may be embedded into the material of the lead body 106. In one embodiment, the lead body 106 defines a lumen 160 for each conductor 152. In another embodiment, two or more conductors 152 (or even all of the conductors) may pass through a single lumen. In at least some embodiments, the conductors may include insulation (or other material) that is color coded to distinguish the conductors, particularly if two or more conductors are in a single lumen. One or more lumens may also be provided within the lead to permit fluidic material (such as a drug) to pass through the lumen to the site of implantation.

In one embodiment, the array of contacts 150 makes up a lead contact array 142 and each of the contacts 150 in the lead contact array 142 preferably corresponds with a contact in a control module contact array 140 to provide electrical coupling between the control module 102 and the lead 106 and its electrodes 148. The array of contacts can similarly make up the electrode 148 of a lead electrode array 144 or any other array of contacts on lead 104; for example, contacts that can be used to connect to corresponding contacts on a lead extension (or the array of contacts may be provided on a lead extension.) Furthermore, each contact 150 of lead contact array 142 does not necessarily correspond to a contact of the control module contact array 140. For example, additional contacts 150 may be provided on the lead contact array 142 for future functionality, expansion, or the like.

Figure 3:
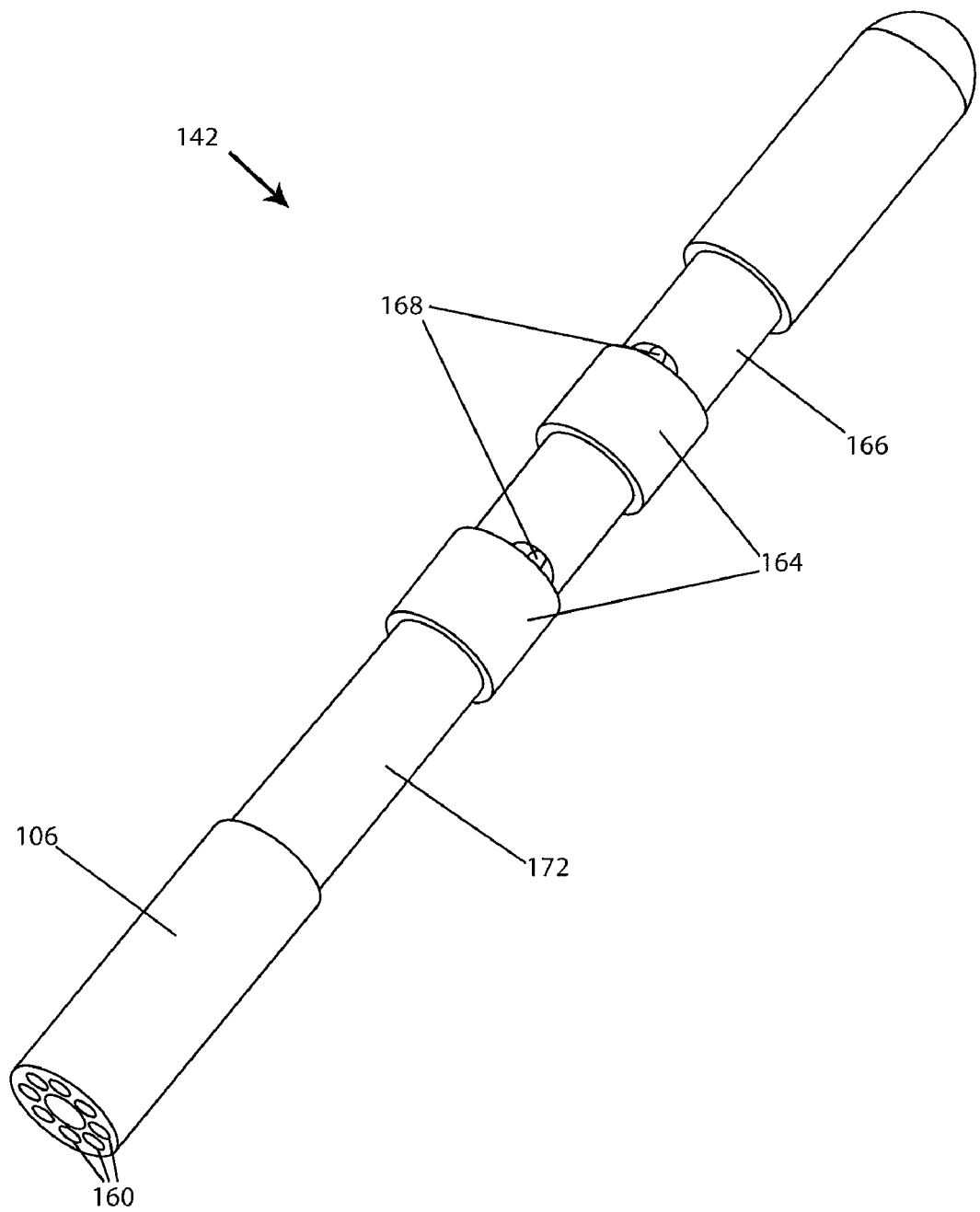
FIG. 3 is a schematic perspective view of a portion of one embodiment of a lead body, according to the invention.

The contacts 150 can be formed, for example, by introducing a conductor 152 into a lumen 160 and extending a portion of conductor 152 outwardly from the lead body 106 through an opening 168 (FIG. 3). The extended portion can then be coiled or otherwise wrapped around the lead body 106 to form contact 150. In some embodiments, an assembly fixture is used to maintain tension on the conductor 152 during coiling. The amount of tension can be varied based upon factors such as, for example, the material of the conductor, the diameter of the lead body, the desired coil diameter, or the like. After the conductor 152 is coiled, any excess portion of the conductor 152 that remains may be removed by trimming, cutting, clipping, or the like. Preferably, the excess portion removed after the conductor is secured to the lead body using adhesive or other securing methods.

The conductors 152 (and contacts 150 made using the conductors 152) can be made of any conductive material. Examples of suitable materials include metals, alloys, conductive polymers, conductive carbon, and the like, as well as combinations thereof. The conductors 152 are preferably made of a conductive material suitable for contact with biological tissue and fluids when implanted. In one embodiment, a portion of the conductor 152 is insulated with an insulating material disposed over the portion. For example, the portion of the conductor 152 within the lumen 160 may be insulated. The portion of the conductor 152 forming the contact 150 is typically not insulated. Insulation, if any, on this portion of the conductor can be removed using any method including, but not limited to, grinding the conductor as described below or any other suitable mechanical or chemical removal method.

Each contact 150 may be of any suitable length and diameter and can be placed at any suitable location along the lead body 106. Typically, the contacts will be positioned at, or near, either the distal or proximal ends of the lead body or both. As one example, the contacts 150 may be spaced at a uniform distance along the longitudinal axis of lead body 106 near the proximal or distal end of the lead. Alternatively, the contacts 150 may be spaced non-uniformly. The diameter and length of each contact 150 can be the same or different. Any suitable number of contacts 150 in either the lead contact array 142 or lead electrode array 144 can be selected. For example, there can be two, four, six, eight, ten, twelve, fourteen, sixteen, or more contacts 150. Other even or odd numbers of contacts 150 may be used.

Optionally, lead 104 may include a retention sleeve 170 at the proximal end to improve the attachment of the lead 104 to the control module 102 (or a lead extension). The retention sleeve 170 may have texture and pliability characteristics such that it acts like a gasket to prevent or restrict moisture from entering the control module 102. Alternatively or additionally, the retention sleeve 170 may be shaped, designed, or textured such that insertion of the lead 104 into the control module 102 couples the lead/control module assembly such that the likelihood of unintentional detachment of the lead 104 from the control module 102 is reduced.

Figure 4:
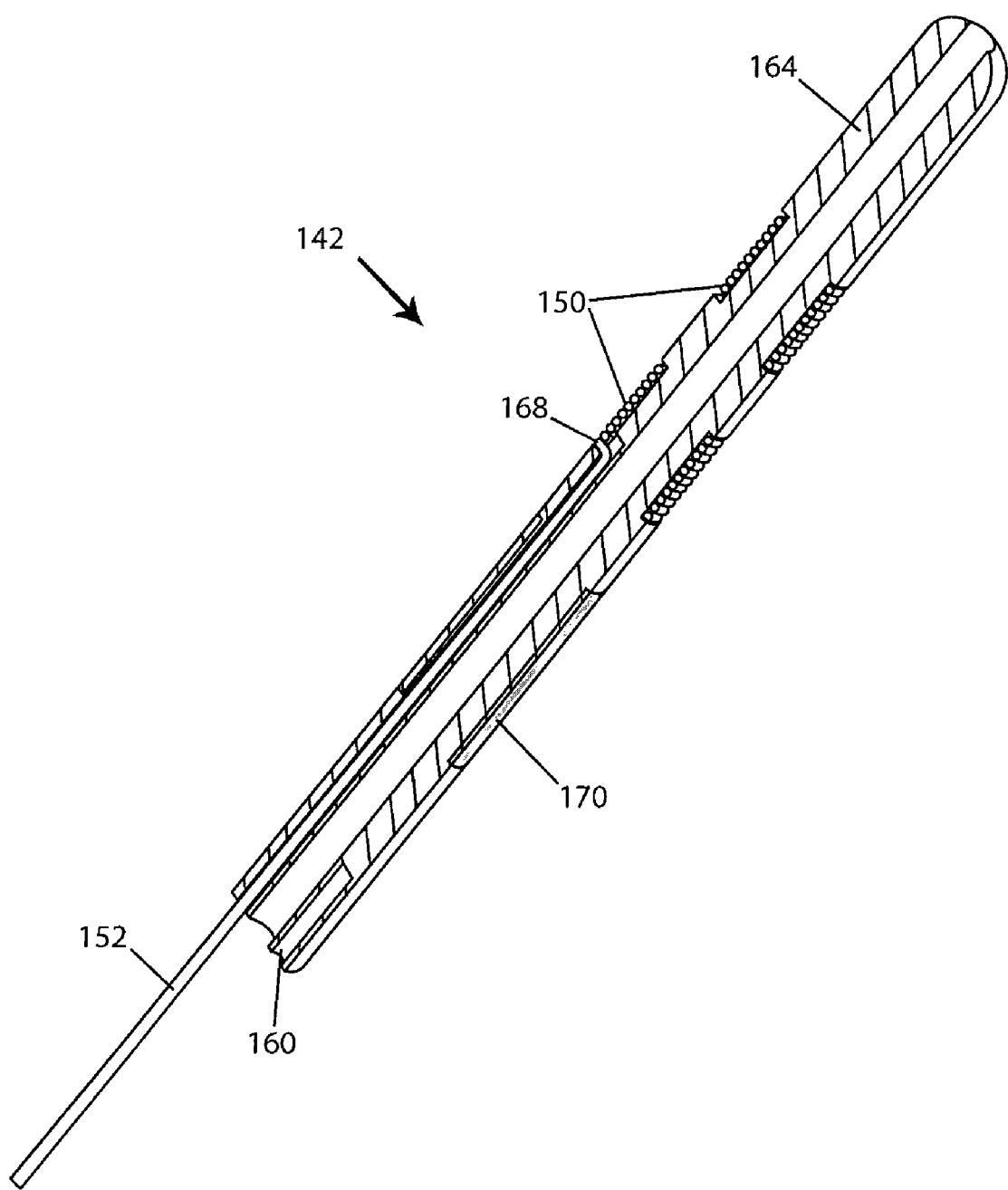
FIG. 4 is a schematic cut-away side view of a portion of one embodiment of a lead, according to the invention.

FIG. 3 is a perspective view of a portion of the proximal end of one embodiment of a lead body 106, according to the invention. FIG. 4 is a cut-away side view of a portion of the proximal end of one embodiment of a lead 104. The lead body 106 defines non-indented regions 164, recesses 166, openings 168, and an optional retention sleeve indent 172.

The lead body 106 can be made of any biocompatible material and is typically an insulative material. Examples of suitable insulative materials include, but are not limited to, silicone, polyurethane, polyetheretherketone (PEEK), epoxy, Teflon™, nylon, Mylar, other non-conductive polymers, and composite materials, and the like or combinations thereof. As indicated above, the lead body 106 can also define one or more lumens 160 through which the conductors pass or through which a drug or other medication can pass to the site of stimulation near the lead electrode array 144.

The lead body 106 may be formed in the desired shape by any process including, for example, molding (including injection molding, ultrasonic compression molding, and thermal molding), extrusion, casting, laser ablation, or the like. For example, the lead body 106 may be molded with recesses 166.

In at least some embodiments, the lead body 106 is at least initially formed in a cylindrical shape with substantially uniform outer diameter. For example, the lead body 106 can be formed by extruding a multi-lumen body. If desired, the cylindrical lead body can be reformed to create recesses 166 into which contacts 150 can be formed. For example, the portions of the lead body 106 can be compressed, for example using a thermal or ultrasonic compression die, or cut to create the recesses 166.

Thermal or ultrasonic compression can be accomplished by, for example, directing thermal energy or ultrasonic energy, respectively, to heat the lead body 106 and increase the plasticity or malleability of the lead body 106. Mechanical or other compression can be applied to the lead body 106 during heating, after the lead body 106 is sufficiently plastic or malleable to create the recesses 166. Compression may be applied or maintained for any length of time, either for a short duration, or until the plasticity or malleability of the lead body 106 has sufficiently decreased, or the like. Either portions of the lead body 106 or the entire lead body 106 can be heated and compressed as suitable for a given embodiment.

During the reforming process, the shape of internal lumens 160 can be maintained, in at least one embodiment, by use of wire mandrels. These wire mandrels can be inserted and removed through either the proximal or distal ends of the lead body 106.

Openings 168 can be formed by drilling, punching, cutting, ablating, or the like, to create a passage through the lead body 106 to a lumen 160. The openings 168 are typically formed in, or near, the recesses 166, but could also be formed at other suitable locations. The openings 168 can be of any suitable shape and size through which the conductors 152 can pass. In at least some embodiments, the openings 168 are round or oval.

Each recess 166 can be associated with one or more openings 168. If a recess 166 includes multiple openings 168, the openings 168 can be spaced in any arrangement including symmetrical and non-symmetrical arrangements. In one embodiment, each opening 168 is aligned with at least one lumen 160 and defines a passage for a conductor 152 between a lumen 160 and a recess 166. A suitably sized opening 168 may also by aligned with more than one lumen 160 such that opening 168 defines a passage between multiple lumens 160 and a recess 166.

In at least one embodiment, the non-indented regions 164 and recesses 166 serve to place or retain the contacts 150 at the desired locations along lead body 106. In other embodiments, annular spacers or other components, that fit over the lead body and between the contacts 150, may be used in conjunction with an isodiametric lead body 106 to accomplish similar objectives without requiring the formation of recesses. In yet other embodiments, the contacts 150 can be formed over a non-indented region of the lead body 106 and without a spacer.

Figure 5A:
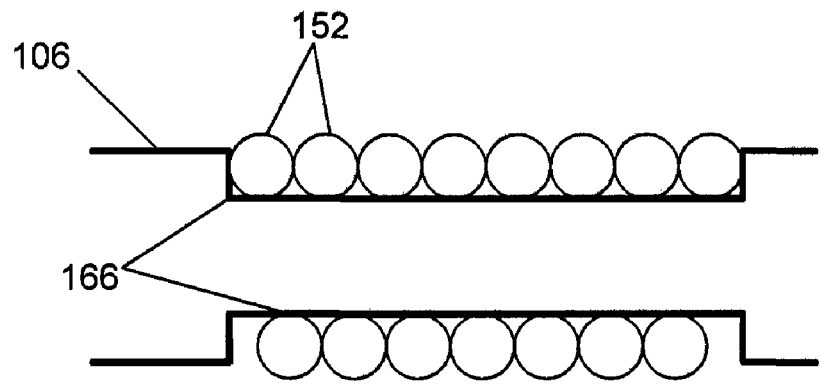
FIG. 5A is a schematic cross-sectional view of one embodiment of a portion of a lead and a contact, according to the invention.
Figure 5B:
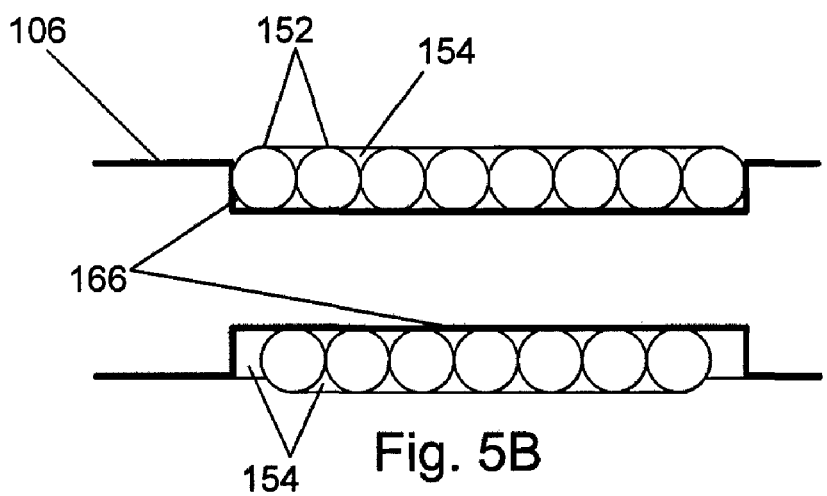
FIG. 5B is a schematic cross-sectional view of another embodiment of a portion of a lead and a contact, according to the invention.
Figure 5C:
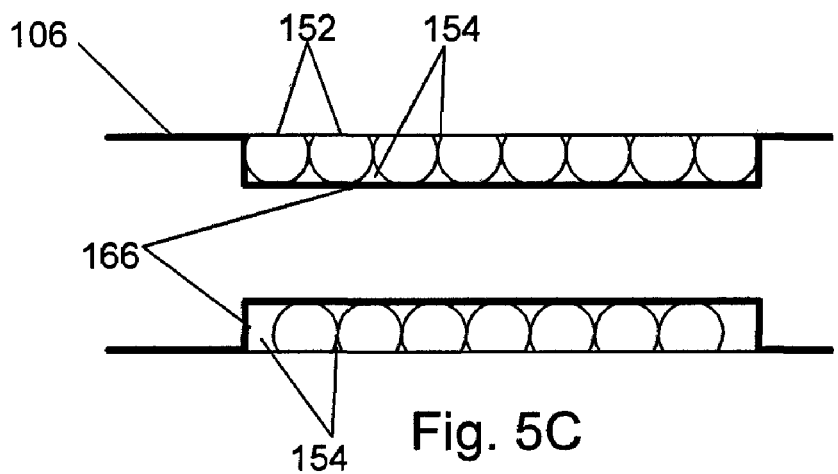
FIG. 5C is a schematic cross-sectional view of yet another embodiment of a portion of a lead and a contact, according to the invention.

FIGS. 5A-5C are cross-sectional views of different embodiments of a portion of a lead body 106 with contacts 150. In one embodiment, as illustrated in FIG. 5A, the conductor 152 has been coiled around the lead body 106 to form the contact 150. After coiling, the contact 150 is ready for use in at least some applications. For other applications, the conductor 152 may be optionally bonded to the lead body 106 by any method including, for example, resistance welding, laser welding, adhesive (e.g., conductive epoxy), or the like. Preferably, the conductor 152 is attached to the lead body 106 by a method that results in a durable attachment of the conductor 152 to the lead body 106 under expected usage conditions.

For yet other applications, the coiled conductor 152 may be encapsulated with a potting compound 154, as shown in FIG. 5B. The potting compound 154 may be any suitable conductive or non-conductive material. In at least one embodiment, the potting compound 154 is a flexible encapsulate such as silicone (e.g., room temperature vulcanizing silicone), adhesive, or the like. The potting compound 154 may be electrically conductive.

For yet further applications, the encapsulated contact 150 may be ground after encapsulation (or even without encapsulation), as shown in FIG. 5C, to expose a portion of the conductor 152. Grinding of the conductor 152 and the potting compound 154 can be accomplished using any grinding method known in the art. In one embodiment, centerless grinding is employed to produce a suitable smooth surface on the contact 150. In at least some embodiments, the contact 150 is ground to be substantially isodiametric with the adjacent portions of the lead body 106. However, it is recognized that in certain applications it may be beneficial to have non-isodiametric contacts 150.

Turning again to FIG. 1, the lead 104 extends from the control module 102 (or from one or more lead extensions coupled to the control module) to conduct electrical pulses from the control module to the electrodes 148. The control module 102 typically includes a housing 114 with an electronic subassembly 110 and, in at least some embodiments, a power source 120 disposed within a chamber in the housing.

Preferably, the housing 114 is resistant to moisture penetration into the chamber containing the electronic subassembly 110 and the power source 120. In some embodiments, water may diffuse through the housing 114. Preferably, the diffused water is relatively pure, without substantial ionic content, as deionized water is relatively non-conductive. The housing 114 may be made of any biocompatible material including, for example, glass, ceramics, metals, and polymers, as well as combinations thereof. Preferably, the material of the plastic housing is a hydrophobic polymer material. The housing 114 may include additives such as, for example, fillers, plasticizers, antioxidants, colorants, and the like. The thickness of the walls of the housing 114 may also impact the moisture permeability of the housing 114. A minimum thickness needed to achieve a particular degree of resistance to moisture transport will often depend on the material selected, as well as any additives.

Optionally, the housing 114 and the lead body 106 (or both) can be covered, in full or in part, with a coating. The coating can be provided to improve or alter one or more properties of the housing 114 or the lead body 106 including, for example, biocompatibility, hydrophobicity, moisture permeability, leaching of material into or out of the housing, and/or the like. In one embodiment, a coating can be applied which contains a compound, such as, for example, a drug, prodrug, hormone, or other bioactive molecule, that can be released over time when the control module 102 and the lead 104 are implanted.

In another embodiment, the housing 114 or the lead 104 itself may include such a compound to be released over time after implantation.

Figure 6:
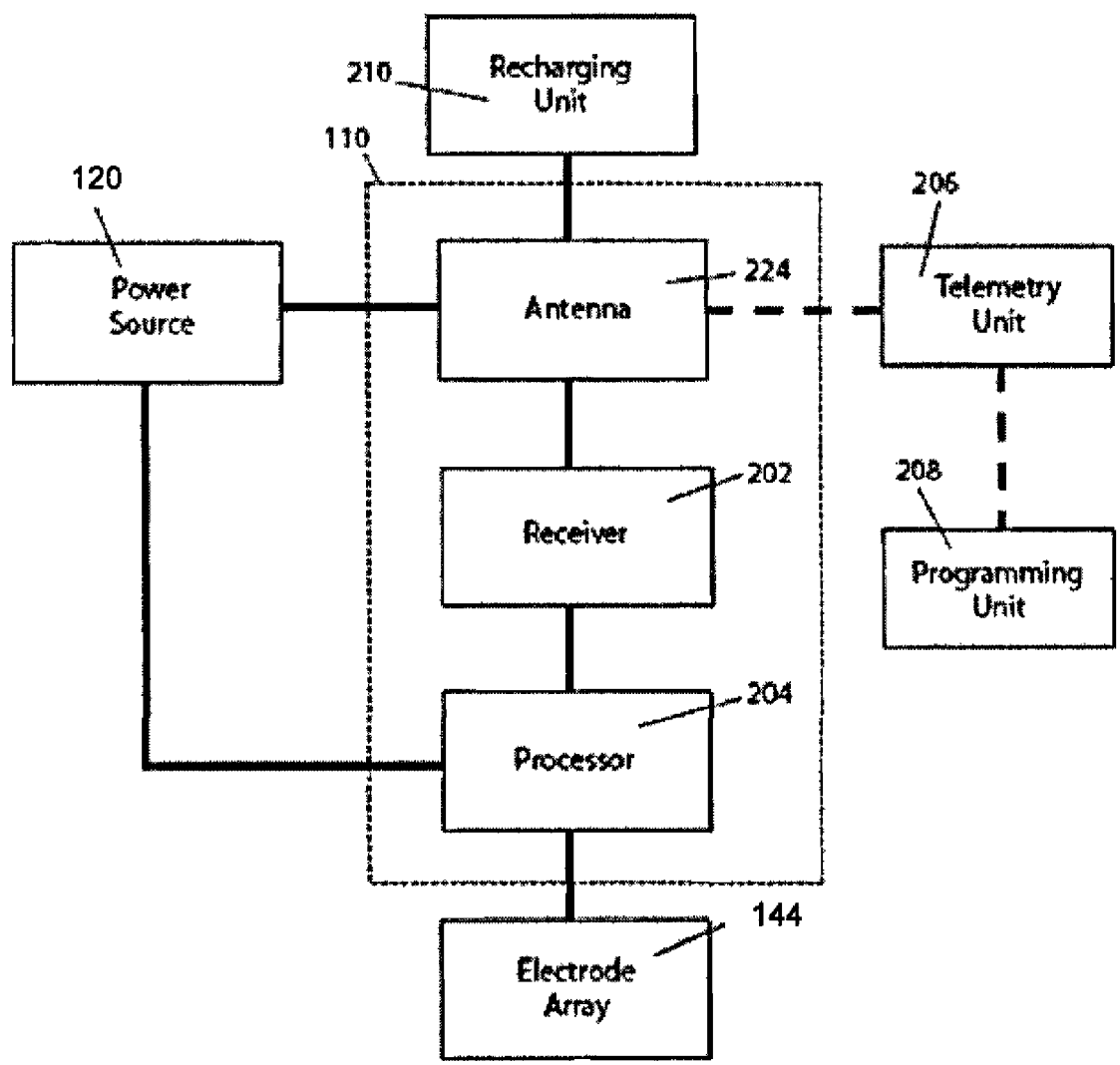
FIG. 6 is a schematic block diagram of one embodiment of a stimulation system, according to the invention.

FIG. 6 is a schematic overview of one embodiment of components of a system for stimulation, including the electronic subassembly 110 and the power source 120. It will be understood that the system for stimulation and electronic subassembly 110 can include more, fewer, or different components and can have a variety of different configurations including those configurations disclosed in the stimulation system references cited herein. Some or all of the components of the electronic subassembly can be positioned on one or more circuit boards or similar carriers within the housing 114 of the control module 102, if desired.

Any power source 120 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via optional antenna 224 or a secondary antenna (not shown). The external power source can be in a device that is mounted on the skin of the user or in a unit that is provided near the control module user on a permanent or periodic basis.

If power source 120 is a rechargeable battery, the battery may be recharged using the optional antenna 224, if desired. Power can be provided to the battery for recharging by inductively coupling the battery through the antenna 224 to a recharging unit 210 external to the user. Examples of such arrangements can be found in the stimulation system references identified above.

In one embodiment, electrical current is emitted from the lead electrode array 144 to stimulate motor nerve fibers, muscle fibers, or other body tissues. The electronic subassembly 110 provides the electronics used to operate the stimulation system and generate the electrical pulses at the lead electrode array 144 to produce stimulation of the body tissues.

In the illustrated embodiment, the processor 204 is generally included in the electronic subassembly 110 to control the timing and electrical characteristics of the stimulation system. For example, the processor 204 can, if desired, control one or more of the timing, frequency, strength, duration, and waveform of the pulses. In addition, the processor 204 can select which of electrodes of the electrode array 144 is to be used to provide stimulation, if desired. In some embodiments, the processor 204 may select which electrodes are cathodes and which electrodes are anodes. In some embodiments, a testing procedure using various combinations of electrodes can be used to identify which electrodes provide the most useful stimulation of the desired tissue. This process may be performed using an external programming unit 208, as described below, that is in communication with the processor 204.

Any processor 204 can be used. For example, the processor 204 can be as simple as an electronic device that produces pulses at a regular interval or the processor 204 can be complex and capable of receiving and interpreting instructions from the external programming unit 208 to allow modification of pulse characteristics. In the illustrated embodiment, the processor 204 is coupled to a receiver 202 which, in turn, is coupled to an optional antenna 224. This allows the processor 204 to receive instructions from an external source to direct the pulse characteristics and the selection of the electrodes, if desired.

In one embodiment, the antenna 224 is capable of receiving signals (e.g., RF signals) from an external telemetry unit 206 which is programmed by an external programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit 206 may not be worn or carried by the user but may only be available at a home station or at a clinician's office. The programming unit 208 can be any unit that can provide information to the telemetry unit 206 for transmission to the stimulation system. The programming unit 208 can be part of the telemetry unit 206 or can provide signals or information to the telemetry unit 206 via a wireless or wired connection. One example of a suitable programming unit 208 is a computer operated by the user or clinician to send signals to the telemetry unit 206.

The signals sent to the processor 204 via the antenna 224 and the receiver 202 can be used to modify or otherwise direct the operation of the stimulation system. For example, the signals may be used to modify the pulses of the stimulation system such as modifying one or more of pulse duration, pulse frequency, pulse waveform, and pulse strength. The signals may also direct the stimulation system to cease operation or to start operation or to start charging a battery. In other embodiments, the electronic subassembly 110 does not include an antenna 224 or a receiver 202 and the processor 204 operates as programmed prior to implantation.

Optionally, the stimulation system may include a transmitter (not shown) coupled to the processor 204 and the antenna 224 for transmitting signals back to the telemetry unit 206 or another unit capable of receiving the signals. For example, the stimulation system may transmit signals indicating whether the stimulation system is operating properly or not or indicating when a battery needs to be charged. The processor 204 may also be capable of transmitting information about the pulse characteristics so that a user or clinician can determine or verify the characteristics.

The optional antenna 224 can have any form. In one embodiment, the antenna 224 includes a coiled wire that is wrapped at least partially around the electronic subassembly 110 within or on the housing 114.

Any suitable method of manufacture of the components of the system for stimulation can be used.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead comprising:
    an elongated lead body of non-conductive material, the lead body comprising a distal portion and a proximal portion; and
    a plurality of conductive wires, each wire comprising a first portion disposed within the lead body and a second portion extending out of the proximal portion of the lead body, wherein the second portion is coiled around the lead body to form a one of a plurality of contacts on the outer surface of the lead, wherein one of the plurality of contacts consists of the second portion, and wherein the contacts are configured and arranged to electrically couple the lead to a control module, wherein each of the plurality of contacts is formed using only one of the plurality of conductive wires.

2. The lead of claim 1, wherein the lead body comprises a plurality of indented regions, and wherein the second portions of the conductive wires are individually coiled around respective portions of the indented regions.

3. The lead of claim 2, wherein the respective contacts are isodiametric with respect to a non-indented region of the lead body adjacent to at least one of the indented regions.

4. The lead of claim 1, further comprising an adhesive that bonds the second portions of the conductive wires to the proximal portion of the lead body.

5. The lead of claim 1, wherein the lead body defines a plurality of lumens, and wherein each conductive wire of the plurality of conductive wires is disposed within a one of the lumens.

6. The lead of claim 1, wherein the plurality of conductive wires further comprise a third portion coiled around the lead body to form a contact on the outer surface of the lead configured to be an electrode suitable to stimulate body tissue.

7. The lead of claim 1, wherein the lead body defines at least one retention sleeve indent configured for receiving at least one retention sleeve and the lead further comprises a retention sleeve disposed in the retention sleeve indent.

8. A stimulation system comprising:
the lead of claim 1; and
a control module coupleable to the lead, wherein the control module is arranged to provide electrical signals to the contact.

9. The stimulation system of claim 8, wherein the lead and control module are implantable.

10. The stimulation system of claim 8, wherein the system is configured to provide spinal cord stimulation.

11. A method of producing the lead of claim 1, comprising:
disposing each of the plurality of conductive wire within, and along, the elongated lead body with the second portion of the wire extending through an opening at, or near, the proximal portion of the lead body; and
coiling the second portion of the conductive wire around the lead body to form a one of the plurality of contacts.

12. The method of claim 11, further comprising forming an indented section on the lead body.

13. The method of claim 12, wherein forming an indented section on the lead body comprises applying compression to the lead body to form an indented section; and forming the opening in the indented section.

14. The method of claim 13, wherein the lead body defines a lumen and forming an indented section on the lead body further comprises disposing a wire mandrel into the lumen prior to, and while, applying compression to the lead body.

15. The method of claim 13, wherein forming an indented section on the lead body further comprises heating a portion of the lead body with thermal energy.

16. The method of claim 13, wherein forming an indented section on the lead body further comprises heating a portion of the lead body with ultrasonic energy.

17. The method of claim 11, further comprising bonding the contacts to the elongated body.

18. The method of claim 11, further comprising grinding the contacts to form smooth contacts.

19. The method of claim 11, further comprising centerless grinding the contacts to form smooth contacts.

* * * * *